US00PP28151P2

(12) United States Plant Patent
Zaiger et al.

(10) Patent No.: US PP28,151 P2
(45) Date of Patent: Jul. 4, 2017

(54) INTERSPECIFIC TREE NAMED 'RICH MAGIC'

(50) Latin Name: **Interspecific *Prunus* species**
Varietal Denomination: Rich Magic

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 14/999,265

(22) Filed: Apr. 18, 2016

(51) Int. Cl.
*A01H 5/08* (2006.01)

(52) U.S. Cl.
USPC ..... Plt./180

(58) Field of Classification Search
USPC ..... Plt./180
CPC ..... A01H 5/0837
See application file for complete search history.

*Primary Examiner* — Kent L Bell

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with a vigorous, upright growth habit.
2. Regular and productive bearer of large size, yellow flesh fruit.
3. Fruit with a high degree of attractive red skin color.
4. Fruit with very good flavor and eating quality.
5. Fruit with good handling and shipping quality.

1 Drawing Sheet

Botanical designation: Interspecitic *Prunus* species.
Variety denomination: 'Rich Magic'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

Prior Varieties

Among the existing varieties of nectarine, peach and interspecific trees, which are known to us, and mentioned herein, 'Honey Lite' Nectarine (U.S. Plant Pat. No. 18,400), 'Super Lady' Peach (U.S. Plant Pat. No. 15,578), the proprietary non-patented peach seedling selection '57Z684' and the proprietary non-patented interspecific seedling selections '53ZA915' and '53ZE476'.

STATEMENT REGARDING FEDERALLY SPONSORED RESEARCH AND DEVELOPMENT

Not applicable.

ORIGIN OF THE VARIETY

The new and distinct variety of interspecific tree was developed by us in our experimental orchard located near Modesto, Calif. from a first generation cross between our proprietary non-patented interspecific seedling '53ZE476' and 'Honey Lite' Nectarine (U.S. Plant Pat. No. 18,400). The seed parent (53ZE476) originated from a cross between our proprietary non-patented peach seedling '57Z684' and our proprietary non-patented interspecific seedling '53ZA915'. A large number of these first generation seedlings were grown and budded to older trees of 'Nemaguard' Rootstock (non-patented) to accelerate rapid fruit production. Under close and careful observation we recognized the desirable tree and fruit characteristics of the present seedling and selected it in 2008 for additional asexual propagation and commercialization.

ASEXUAL REPRODUCTION OF THE VARIETY

In 2008 asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new and distinct variety of interspecific tree is of large size, vigorous, upright growth and a regular and productive bearer of large size, yellow flesh, clingstone fruit. The fruit is further characterized by its attractive red skin color, very good flavor and eating quality with good handling and storage ability. In comparison to its non-patented interspecific seed parent (53ZE476) the fruit of the new variety has yellow flash compared to white. In comparison to its pollen parent 'Honey Lite' Nectarine (U.S. Plant Pat. No. 18,400) the fruit of the new variety is a peach compared to a nectarine and is approximately 10 days earlier in maturity. In comparison to the commercial variety 'Super Lady' Peach (U.S. Plant Pat. No. 15,578) the fruit of the new variety is larger in size and is approximately 22 days later in maturity.

DESCRIPTION OF THE PHOTOGRAPH

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 7 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 7 year old specimens grown near Modesto, Calif., with color in accordance with Munsell Book of Color published in 1958.

Tree:

*Size*.—Large, usually pruned to 3 to 3.5 meters in height and width for economical harvesting of fruit. Size varies with different cultural practices.

*Vigor*.—Vigorous, growth of 1.5 to 2 meters the first growing season. Varies slightly with type and fertility of soil, climatic conditions and cultural practices.

*Form*.—Upright, usually pruned to vase shape.

*Branching habit*.—Upright, crotch angle approximately 30°, increases with heavy crop load.

*Productivity*.—Productive, thinning and spacing of fruit necessary for desired market size fruit. Number of fruit set varies with climatic conditions during blooming period.

*Bearer*.—Regular, has had adequate fruit set 5 consecutive years. No alternate bearing observed.

*Fertility*.—Self fertile.

*Density*.—Medium dense, usually pruned to vase shape to increase air movement and sunlight to enhance fruit color and health of fruit wood.

*Hardiness*.—Hardy in all stone fruit growing areas of California. Tree grown in USDA Hardiness Zone 9. Winter chilling requirement approximately 700 hours at or below 45° F.

Trunk:

*Size*.—Large, average circumference 53.3 cm at 25.4 cm above ground on a 7 year old tree.

*Stocky*.—Medium stocky.

*Texture*.—Medium shaggy, roughness increases with age.

*Color*.—Varies from 10YR 2/2 to 10YR 3/2.

Branches:

*Size*.—Medium. Average circumference 13.7 cm at 1.2 meters above ground. Crotch angle approximately 30°, increases with heavy crop load.

*Surface texture*.—New growth relatively smooth. Mature growth medium rough, roughness increases with age.

*Lenticels*.—Average number 23 in a 25.8 square cm area. Average length 5.7 mm. Average width 2.2 mm. Color varies from 7.5YR 5/8 to 10YR 5/8.

*Color*.—New growth varies from 5GY 6/6 to 5GY 7/6. Mature growth varies from 7.5YR 3/4 to 10YR 4/2, varies with age of growth.

Leaves:

*Size*.—Large. Average length 105.7 mm. Average width 32.3 mm.

*Form*.—Lanceolate.

*Apex*.—Acuminate.

*Base*.—Cuneate.

*Margin*.—Serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 8.0 mm. Average width 1.8 mm. Longitudinally grooved. Surface — glabrous. Color varies from 2.5GY 5/8 to 2.5GY 6/8.

*Glands*.—Type — reniform. Size — medium. Average length 1.2 mm. Average diameter 1.1 mm. Number varies from 1 to 3, average number 2. Located primarily on base of leaf blade and upper portion of petiole. Color varies from 10R 2/4 to 7.5YR 2/2.

*Stipules*.—Average number 2. Average length 6.7 mm. Edges — pectinate. Color varies from 10Y 5/6 to 5GY 5/8.

*Color*.—Upper surface varies from 2.5GY 5/6 to 5GY 5/6. Lower surface varies from 5GY 4/4 to 2.5GY 5/4. Midvein color varies from 10Y 7/6 to 2.5GY 7/6.

Flower buds:

*Size*.—Large. Average length 24.3 mm. Average diameter 13.1 mm.

*Hardiness*.—Hardy with respect to California winters.

*Density*.—Dense.

*Form*.—Conical, becoming elongated just before opening.

*Pedicel*.—Small to medium. Average length 4.6 mm. Average width 1.5 mm. Surface — glabrous. Color varies from 7.5GY 6/6 to 7.5GY 6/8.

*Color*.—Varies from 7.5RP 6/8 to 7.5RP 7/8.

Flowers:

*Blooming period*.—Date of First Bloom Feb. 7, 2015. Date of Petal Fall Feb. 17, 2015, varies slightly with climatic conditions.

*Size*.—Large, showy. Average height 21.7 mm. Average diameter 50.5 mm.

*Petals*.—Normally 5, alternately arranged to sepals. Size — large. Average length 25.2 mm. Average width 21.3 mm. Form — obovate. Petal apex — rounded. Petal base — truncate. Margin — sinuate. Arrangement — overlapping. Both upper and lower surfaces glabrous. Color varies from 5RP 8/6 to 5RP 8/8, fades with age of flower.

*Sepals*.—Normally 5, alternately arranged to petals. Size — large. Average length 7.5 mm. Average width 7.0 mm. Shape — ovate. Apex rounded to triangular. Margin — entire. Color — upper surface varies from 7.5GY 6/6 to 7.5GY 6/8. Lower surface varies from 7.5GY 5/6 to 7.5R 2/8. Surface — upper surface glabrous, lower surface pubescent.

*Stamens*.—Average number per flower 41. Average filament length 15.6 mm. On average, the stamens are even with the height of the petals. Filament color N 9.5/(white). Anther color varies from 7.5RP 7/6 to 5Y 8/8.

*Pollen*.—Self fertile. Color varies from 10YR 8/8 to 2.5Y 7/12.

*Pistil*.—Number — normally one. Average length 19.8 mm. Position of stigma even with anthers. Surface — pubescent. Color varies from 2.5GY 8/6 to 2.5GY 7/8.

*Fragrance*.—Wanting.

*Color*.—5RP 8/6.

*Pedicel*.—Average length 4.9 mm. Average width 1.5 mm. Color varies from 7.5GY 6/6 to 7.5GY 6/8.

*Number flowers per flower bud*.—Normally one.

Fruit:

*Maturity when described*.—Firm ripe and ready for consumption.

*Date of first picking*.—May 27, 2015.

*Date of last picking*.—Jun. 7, 2015, varies slightly with climatic conditions.

*Size*.—Large. Average diameter axially 72.7 mm. Average transversely in suture plane 81.8 mm. Average weight 278.3 grams, varies slightly with fertility of the soil, amount of thinning and climatic conditions.

*Form*.—Globose.

*Suture*.—Smooth to slightly lipped.

*Ventral surface*.—Smooth to slightly lipped.

*Apex*.—Retuse.

*Base*.—Retuse.

*Stem cavity*.—Rounded to slightly elongated in suture plane. Average depth 13.1 mm. Average diameter 8.5 mm.

Stem:

*Size*.—Medium. Average length 9.0 mm. Average diameter 3.4 mm.

*Color*.—Varies from 10Y 6/6 to 2.5GY 6/8.

Flesh:

*Ripens*.—Evenly.

*Texture*.—Firm, meaty, crisp.

*Fibers*.—Few, small, tender.

*Firmness*.—Very good, comparable to other commercial varieties.

*Aroma*.—Moderate.

*Amydgalin*.—Undetected.

*Eating quality*.—Very good.

*Flavor*.—Very good.

*Juice*.—Moderate amount, enhances flavor.

*Acidity*.—Not available.

*Brix*.—Average Brix 14.6°, varies slightly with amount of fruit per tree and climatic conditions.

*Color*.—Varies from 5Y 8/8 to 5Y 8/10.

*Pit cavity*.—Average length 41.6 mm. Average width 29.3 mm. Average depth 11.8 mm. Color varies from 5Y 7/8 to 5Y 7/10.

Skin:

*Thickness*.—Medium.

*Surface*.—Smooth.

*Pubescence*.—Moderate amount, short in length.

*Tendency to crack*.—None.

*Color*.—Ground color varies from 2.5Y 8.5/10 to 2.5Y 8/10. Overspread with 7.5R 3/10 to 10R 2/4.

*Tenacity*.—Tenacious to the flesh.

*Astringency*.—Undetected.

Stone:

*Type*.—Clingstone, strong adherence to flesh.

*Size*.—Large. Average length 40.6 mm. Average width 28.0 mm. Average thickness 21.3 mm.

*Form*.—Ovoid.

*Base*.—Flat.

*Apex*.—Pointed. Average length 5.5 mm.

*Surface*.—Pitted throughout, pits vary from round to elongated.

*Sides*.—Unequal, one side extending further from suture plane.

*Ridges*.—Relatively smooth, extending from base to apex.

*Tendency to split*.—None.

*Color*.—Varies from 7.5YR 6/6 to 10YR 6/6 when dry.

Kernel:

*Size*.—Medium to large. Average length 20.1 mm. Average width 12.4 mm. Average depth 6.2 mm.

*Form*.—Ovoid.

*Viability*.—Poor, incomplete embryo development.

*Skin color*.—Varies from 5Y 9/4 to 7.5Y 9/4.

Use: Dessert.

*Market*.—Local and long distance.

Keeping quality: Good, held firm in cold storage 2 weeks at 38° to 42° F. without shriveling, internal breakdown of flesh or appreciable loss of flavor.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices. The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

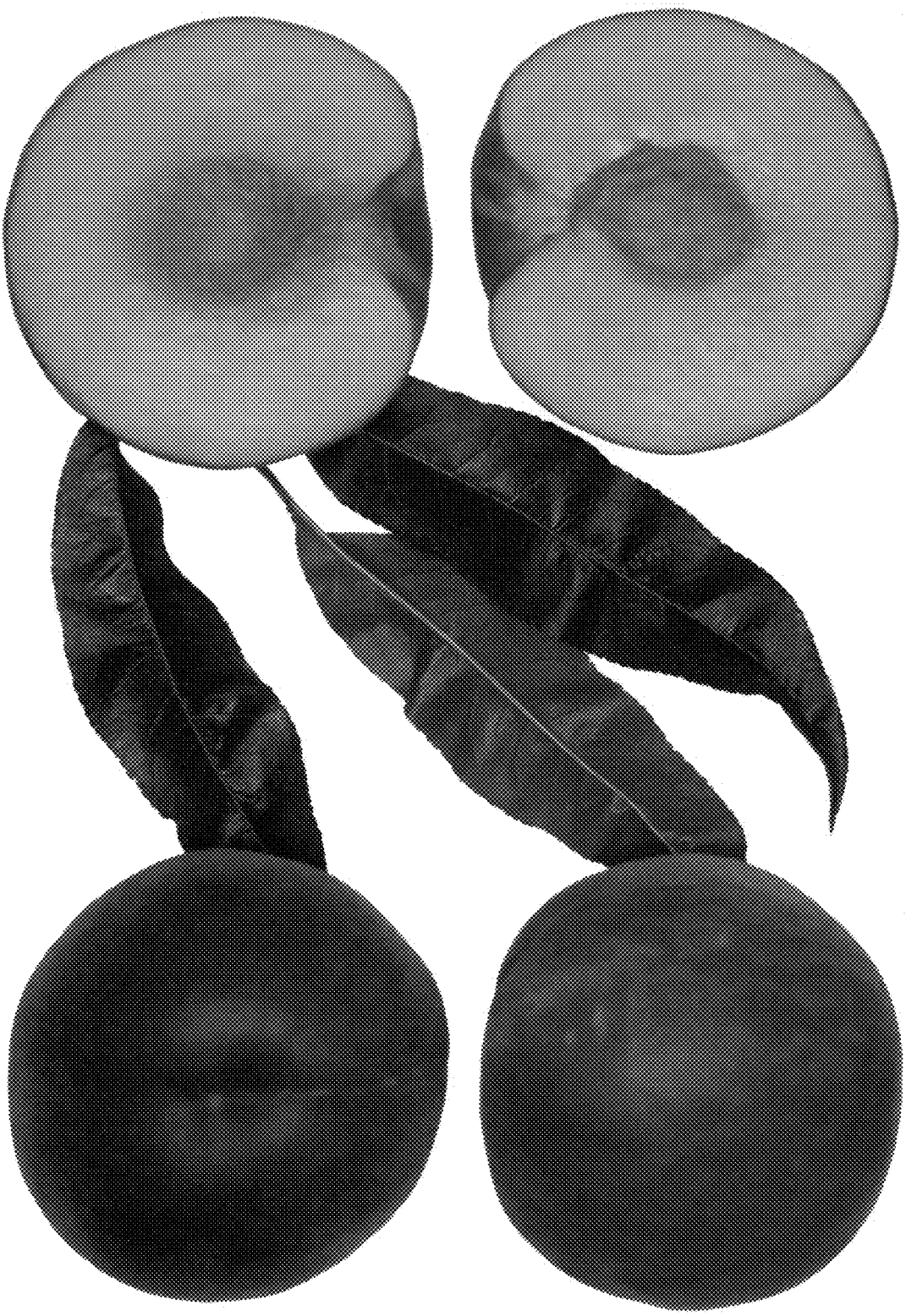

* * * * *